(12) United States Patent
Greenberg et al.

(10) Patent No.: US 8,663,310 B2
(45) Date of Patent: Mar. 4, 2014

(54) HYBRID TYPE A DISSECTION DEVICE

(75) Inventors: Roy K. Greenberg, Bratenahl, OH (US);
Krasnodar Ivancev, London (GB);
David Ernest Hartley, Wannanup (AU)

(73) Assignees: Cook Medical Technologies LLC,
Bloomington, IN (US); The Cleveland Clinic Foundation, Cleveland, OH (US)

( * ) Notice: Subject to any disclaimer, the term of this patent is extended or adjusted under 35 U.S.C. 154(b) by 8 days.

(21) Appl. No.: 13/325,737

(22) Filed: Dec. 14, 2011

(65) Prior Publication Data
US 2012/0158121 A1    Jun. 21, 2012

(30) Foreign Application Priority Data
Dec. 15, 2010    (AU) .................................. 2010254599

(51) Int. Cl.
*A61F 2/06*    (2013.01)

(52) U.S. Cl.
USPC .................. 623/1.13; 623/1.16; 623/1.35

(58) Field of Classification Search
USPC ...................................... 623/1.13, 1.16, 1.35
See application file for complete search history.

(56) References Cited

U.S. PATENT DOCUMENTS

| | | | |
|---|---|---|---|
| 5,902,283 A * | 5/1999 | Darouiche et al. | 604/265 |
| 6,187,033 B1 * | 2/2001 | Schmitt et al. | 623/1.35 |
| 6,645,242 B1 * | 11/2003 | Quinn | 623/1.16 |
| 6,773,457 B2 | 8/2004 | Ivancev et al. | |
| 7,435,253 B1 | 10/2008 | Hartley et al. | |
| 7,488,344 B2 | 2/2009 | Hartley et al. | |
| 7,803,177 B2 | 9/2010 | Hartley et al. | |
| 2002/0156522 A1 * | 10/2002 | Ivancev et al. | 623/1.13 |
| 2004/0073289 A1 * | 4/2004 | Hartley | 623/1.13 |
| 2005/0059923 A1 * | 3/2005 | Gamboa | 604/9 |
| 2007/0043425 A1 | 2/2007 | Hartley et al. | |
| 2007/0088424 A1 | 4/2007 | Greenberg et al. | |
| 2009/0043377 A1 * | 2/2009 | Greenberg et al. | 623/1.35 |
| 2009/0093873 A1 * | 4/2009 | Navia | 623/1.23 |

FOREIGN PATENT DOCUMENTS

WO    2010024879 A1    3/2010

* cited by examiner

*Primary Examiner* — David Isabella
*Assistant Examiner* — Leslie Coburn
(74) *Attorney, Agent, or Firm* — Richard J. Godlewski (57) ABSTRACT

A hybrid stent graft device for treatment of a Type A dissection having a first tubular portion for placement into the ascending aorta and a second tubular portion for extending around the thoracic arch and down the descending aorta is disclosed. The first tubular portion is connectable to the aorta between the sinotubular junction and the brachiocephalic artery so that it essentially replaces the ascending aorta. A temporary bypass tube allows perfusion during an operation. The second tubular portion has an elongate recess outside of the second tubular portion and an aperture defining a fluid flow path into the recess. The recess is intended to engage an outer curve of the thoracic arch to enable blood flow into the arteries of the thoracic arch. An introduction device in combination with the hybrid stent graft described above is also disclosed.

20 Claims, 7 Drawing Sheets

HYBRID TYPE A DISSECTION DEVICE

FIELD OF INVENTION

This invention relates to a medical device and more particularly to a device useful for the treatment of dissection of the aorta.

BACKGROUND

A dissection of the aorta is categorized based on the site of an original intimal tear. A Type A dissection is one which starts in the ascending aorta and may extend to the aortic arch, and possibly the descending aorta. A potential problem with a type A dissection is that it can progress proximally to the heart and may cause problems with heart rhythm.

Treatment involves isolating the heart from the dissected aorta while at the same time providing a blood flow path to the aortic arch and the descending aorta.

DESCRIPTION OF THE INVENTION

In one form, therefore, the invention comprises a hybrid stent graft device for treatment of a Type A dissection, the device comprising a first tubular portion for placement into the ascending aorta and a second tubular portion for extending around the thoracic arch and down the descending aorta, the first tubular portion being connected to the second tubular portion at a junction therebetween;
the first tubular portion comprising a tubular biocompatible graft material defining a first lumen therethrough, the first tubular portion comprising a proximal end and a distal end, the proximal end in use connecting to the aorta substantially at the sinotubular junction and the distal end in use connecting to the aorta proximally of the brachiocephalic artery whereby the first tubular portion essentially replaces the ascending aorta;
a temporary bypass tube of lesser diameter than the first tubular portion and comprising a bypass lumen therethrough, the bypass tube extending from and in fluid communication with the first tubular portion adjacent to the junction between the first tubular portion and the second tubular portion;
the second tubular portion comprising a tubular biocompatible graft material defining a second lumen therethrough and a plurality of self expanding stents along the tubular biocompatible graft material and fastened thereto to support the tubular biocompatible graft material;
the second lumen being in fluid communication with the first lumen through the junction;
the second tubular portion comprising an elongate recess defined by a recess wall and defining a recess lumen, the recess lumen being outside of the second tubular portion and at least one aperture in the recess wall defining a fluid flow path between the second lumen and the recess lumen, the recess lumen in use intended to engage an outer curve of the thoracic arch to enable blood flow from the second lumen through the at least one aperture into the recess lumen and into the arteries of the thoracic arch. Preferably the first tubular portion and the bypass tube comprise a biocompatible corrugated gel seal material.

Preferably the at least one aperture in the recess wall comprises a least one short tube defining the fluid flow path between the second lumen and the recess lumen.

Preferably the flow path comprises two short tubes in the recess wall defining the fluid flow path between the second lumen and the recess lumen.

Preferably the first tubular portion is unstented.

Preferably the recess is substantially boat or bath shaped. The recess wall can comprise reinforcement such that the recess wall and reinforcement comprising a graft material and a wire reinforcement structure.

The hybrid stent graft device can further comprise a second temporary tube, the second temporary tube extending from and in fluid communication with the first tubular portion adjacent to the junction between the first tubular portion and the second tubular portion.

The second temporary tube can comprise a haemoreduction valve to allow access, for instance, for a covered stent graft delivery device to enable the delivery of a covered stent to extend from the at least one aperture or one of the two short tubes to one of the arteries of the thoracic arch.

In an alternative form the invention comprises an introduction device in combination with the hybrid stent graft described above.

In an alternative form, therefore, the invention comprises a hybrid stent graft in combination with an introducer;
the hybrid stent graft being as described above;
the introducer comprising a handle portion, and an introducer portion, the introducer portion comprising a pusher and a nose cone dilator at a distal end of the introducer portion,
the hybrid stent graft being releasably retained on the introducer with the introducer portion extending through the first tubular portion and the second tubular portion with the proximal end of the first tubular portion nearest the handle portion and a distal end of the second tubular portion being releasably retained to the pusher adjacent to the nose cone dilator.

Preferably the second tubular portion comprises diameter reducing ties therealong and a release arrangement for the diameter reducing ties on the handle portion.

Preferably the second tubular portion comprises a releasable spiral stabilising wire engaging the second tubular portion to the pusher and a release arrangement for the releasable spiral stabilising wire on the handle portion.

Preferably the pusher comprises a preformed curve approximating the curvature of the thoracic arch.

It will be seen that by this invention there is provided a hybrid stent graft in which a first part is surgically joined to the sinotubular junction at one end and to the aortic arch at the other and a second part which can be deployed into the descending aorta by endovascular techniques to ensure blood flow to the great vessels of the aortic arch and to the descending aorta. The introducer holds the stent graft while it is being deployed into the descending aorta.

Throughout this specification the term distal with respect to a portion of the aorta, a deployment device or a prosthesis means the end of the aorta, deployment device or prosthesis in use which is further away in the direction of blood flow away from the heart and the term proximal means the portion of the aorta, deployment device or end of the prosthesis in use which is nearer to the heart. When applied to other vessels similar terms such as caudal and cranial should be understood.

BRIEF DESCRIPTION OF THE DRAWINGS

This then generally describes the invention but to assist with understanding reference will now be made to the accompanying drawings which show one embodiment of a hybrid stent graft according to the present invention and to a delivery device in combination with the hybrid stent graft according to the present invention for introducing the device into the vasculature.

In the drawings.

DESCRIPTION OF PREFERRED EMBODIMENT AND DELIVERY DEVICE

Figure 1:
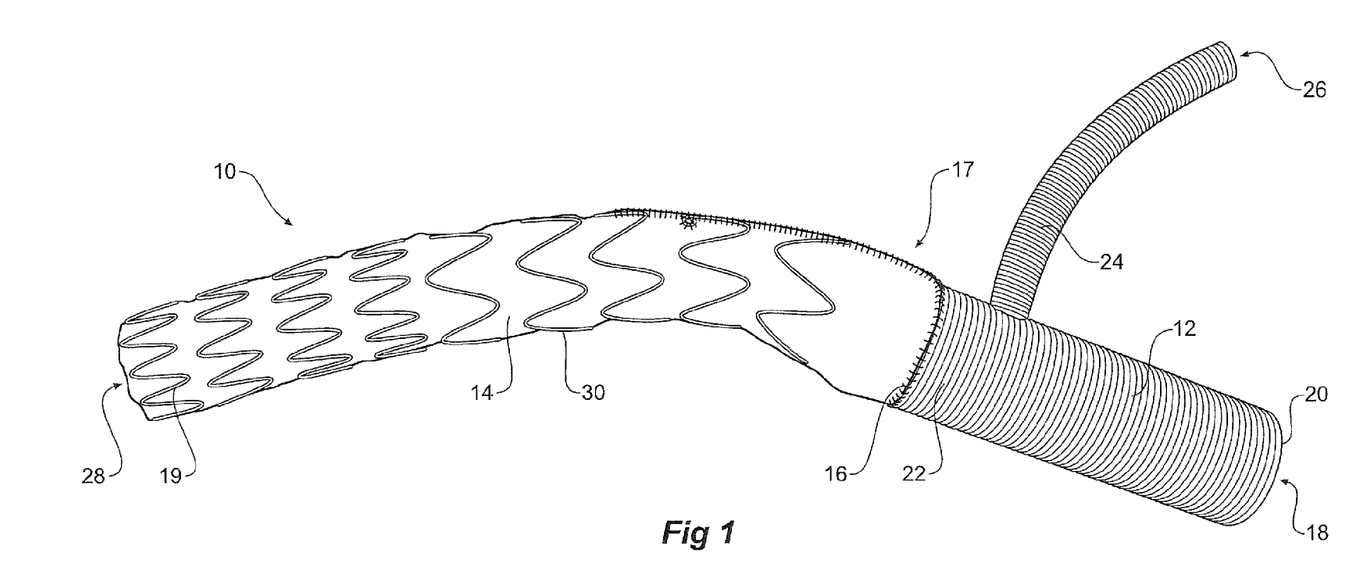
FIG. 1 shows a side view of one embodiment of a hybrid stent graft according to the present invention.
Figure 2:
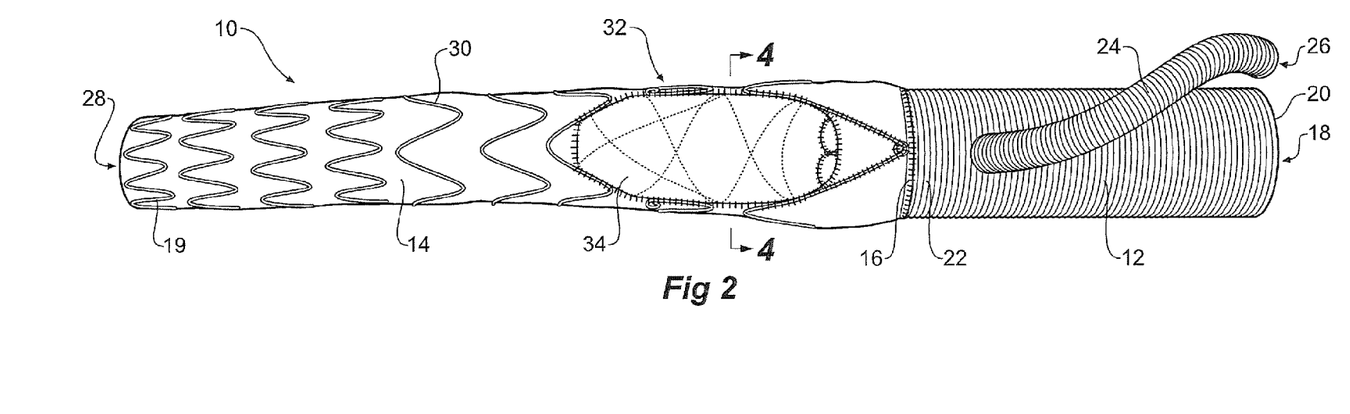
FIG. 2 shows a plan view of one embodiment of the hybrid stent graft shown in FIG. 1.
Figure 3:
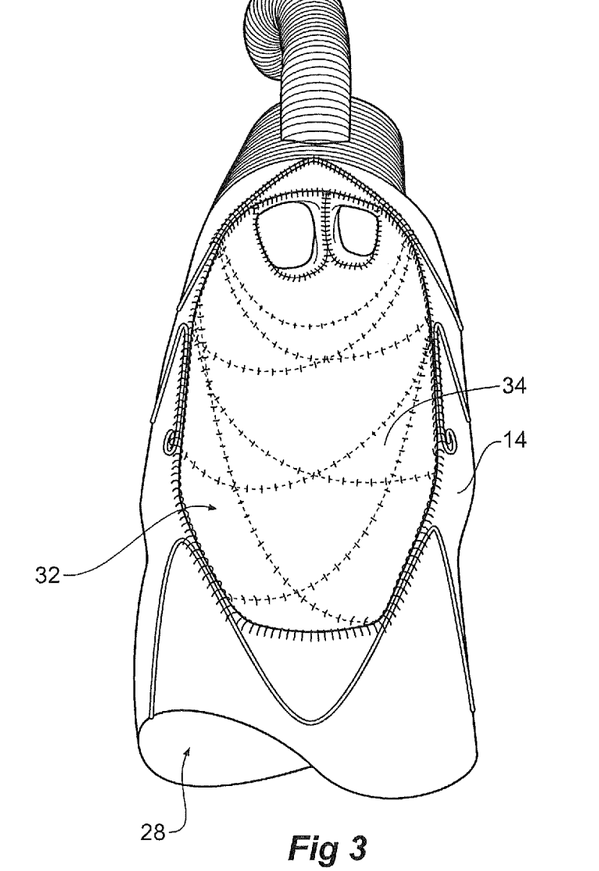
FIG. 3 shows detail of the hybrid stent graft shown in FIG. 1.
Figure 4:
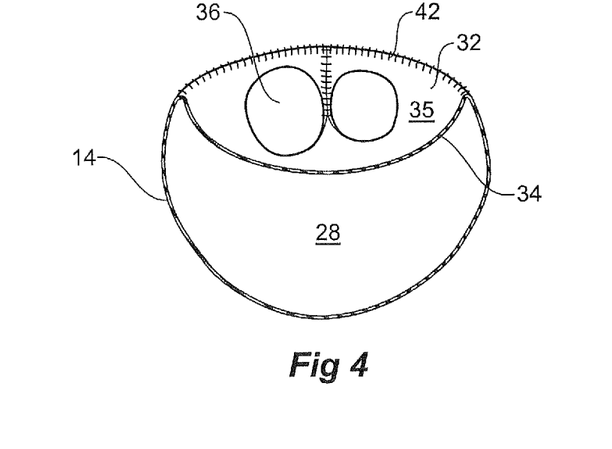
FIG. 4 show as cross sectional view along the line 4-4' in FIG. 2.
Figure 5:
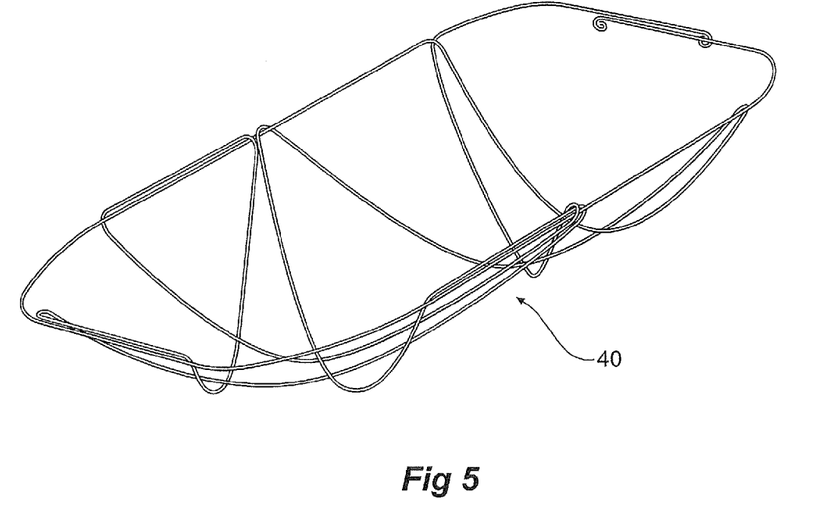
FIG. 5 shows detail of a reinforcement framework for the recess arrangement.
Figure 6:
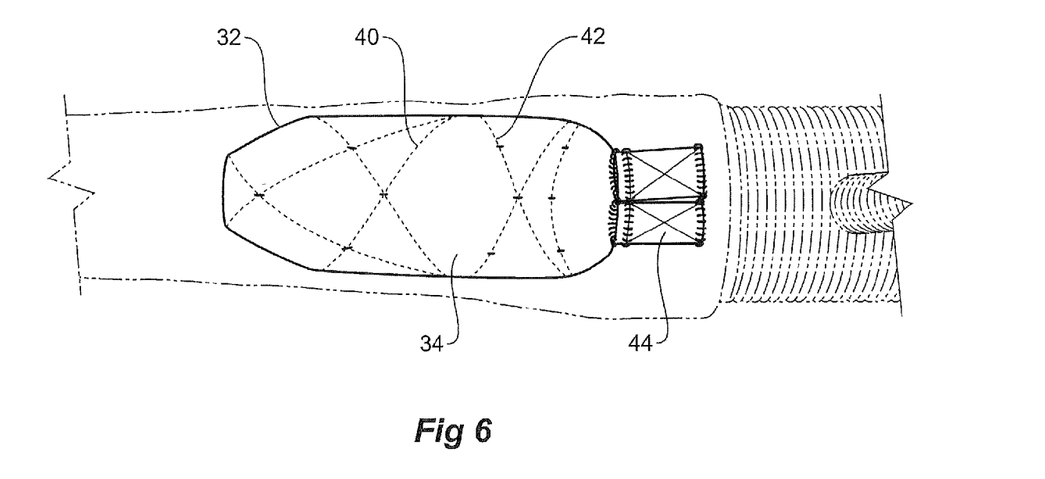
FIG. 6 shows detail of the recess arrangement and short tubes.

FIGS. 1 and 2 show a hybrid stent graft according to one embodiment of the present invention and FIGS. 3 to 6 show detail of various portions of the hybrid stent graft.

In FIGS. 1 and 2 the hybrid stent graft 10 comprises a first tubular portion 12 for placement into the ascending aorta of a patient and a second tubular portion 14 for extending around the thoracic arch and down the descending aorta. The first tubular portion 12 is connected to the second tubular portion 14 at a junction 16.

The first tubular portion 12 comprises a tubular biocompatible graft material which defines a first lumen 18 therethrough. The first tubular portion 12 has a proximal end 20 and a distal end 22. The proximal end in use connects to the aorta substantially at the sinotubular junction and the distal end in use connects to the aorta proximally of the brachiocephalic artery (see FIGS. 8 and 9) such that in use the first tubular portion essentially replaces the ascending aorta of the patient.

A temporary bypass tube 24 of lesser diameter than the first tubular portion has a bypass lumen 26 through it. The bypass tube 24 extends from and is in fluid communication with the first tubular portion adjacent to the junction 16 between the first tubular portion and the second tubular portion.

Both the first tubular portion 12 and the temporary bypass tube 24 are formed from a corrugated biocompatible material which is essentially impervious to blood. Such a material is a gelatine sealed knitter graft material sold under the trade mark Gelseal by Terumo CardioVascular Systems Corp MI, USA.

The second tubular portion 14 comprises a tubular biocompatible graft material and defines a second lumen 28 through it. A plurality of self expanding stents 30 along the tubular biocompatible graft material are fastened to and support the tubular biocompatible graft material. The second lumen 28 is in fluid communication with the first lumen 18 through the junction 16.

The second tubular portion 14 has an elongate recess 32 defined by a recess wall 34 and thereby defines a recess lumen 35. The recess lumen is therefore outside of the second tubular portion. There is at least one aperture 35 in the recess wall defining a fluid flow path between the second lumen 28 and the recess lumen 35. The recess lumen is in use intended to engage an outer curve of the thoracic arch to enable blood flow from the second lumen 28 through the at least one aperture 36 into the recess lumen 35 and into the arteries of the thoracic arch (see FIGS. 8 and 9). Subsequently the pair of tubes 44 can be accessed with bridging covered stents from the brachiocephalic and left common carotid arteries to provide depressurization of the external portion of the stent graft. This will provide a more permanent flow path to the brachiocephalic and left common carotid arteries.

The elongate recess 32 is shown in detail in FIGS. 3 to 6. The recess 32 is supported by a resilient wire framework 40 which is substantially boat shaped or bath shaped and is stitched to the recess wall 34 by stitches 42. In this embodiment the at least one aperture 36 in the recess wall which defines the fluid flow path between the second lumen 28 and the recess lumen 35 is a pair of tubes 44.

The second tubular portion and the recess wall can be formed from a biocompatible graft material such as Dacron.

Figure 7:
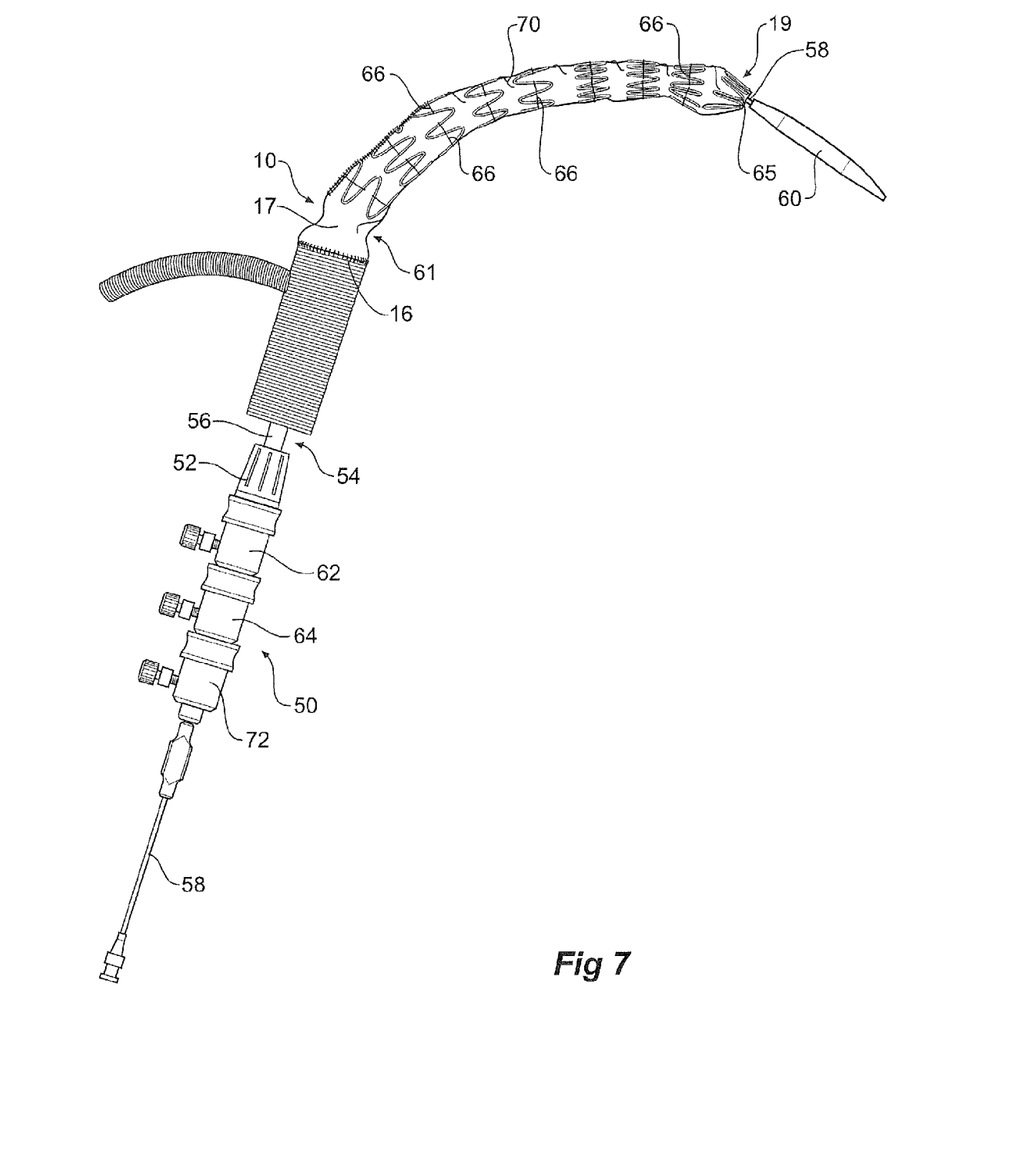
FIG. 7 shows a side view of one embodiment of a hybrid stent graft according to the present invention loaded onto a delivery device.

FIG. 7 shows the hybrid stent graft 10 mounted to a delivery device or introducer 50 for deployment into the descending aorta of a patient. The introducer 50 has a handle portion 52 which in use remains outside a patient and an introduction portion 54. The hybrid stent graft 10 is mounted onto the introduction portion 54. The introduction portion 54 is pre-curved to substantially the curvature of the thoracic arch extending to the descending aorta so that when the introduction portion is introduced into the thoracic arch and extended down into the descending aorta it substantially conforms with the vessel wall.

The introduction portion 54 has a pusher 56 and a guide wire cannula 58 extending through the pusher 56 and extending to a dilator 60 at the distal end of the introducer portion.

The hybrid stent graft 10 is retained onto the introducer portion 54 by several different mechanisms. At a region near the junction 16, the proximal end 17 of the second tubular portion 14 is retained to the pusher 56 by a releasable retention 61 which includes a trigger wire (not shown) which extends back to a trigger wire release 62 on the handle portion. At region near the distal end 19 of the second tubular portion 14 the second tubular portion 14 is retained to the guide wire cannula 58 by a releasable retention 65 which includes a trigger wire (not shown) which extends back also to the trigger wire release 62 on the handle portion. This means that both the proximal end 17 and the distal end 19 of the second portion 14 of the hybrid stent graft 10 can be released when the trigger wire release 62 is withdrawn.

Before the trigger wire release 62 is withdrawn, however, other retention arrangements for the hybrid stent graft must be released. The second portion 14 of the hybrid stent graft 10 is maintained in a diameter reduced condition to hold it in a small enough diameter to be introduced into the descending aorta.

There are provided a number of diameter reducing ties 66 along the length of the second portion 14 of the hybrid stent graft 10. The diameter reducing ties 66 are releasably held by a further trigger wire system with trigger wires (not shown) that extend back to a trigger wire release 64 on the handle portion.

The second portion 14 of the hybrid stent graft 10 is also retained onto the pre-curved guide wire cannula 58 by a spiral wire 70. The spiral wire extends back to a trigger wire release 72 on the handle portion. This helps to hold the second portion into a curved condition.

U.S. Pat. No. 7,803,177 issued 29 Sep. 2010 entitled "Trigger Wire System" discloses trigger wire systems for a stent graft introducer and the teachings therein are incorporated herein in their entirety.

U.S. Pat. No. 7,435,253 issued on Oct. 14, 2008 and entitled "Prosthesis and a Method of Deploying a Prosthesis" discloses a stent graft introducer incorporating retention systems and the teachings therein are incorporated herein in their entirety.

U.S. patent application Ser. No. 11/524,855 filed on Sep. 21, 2006 and entitled "Endoluminal Delivery Assembly" discloses a stent graft introducer incorporating a spiral wire retention system and the teachings therein are incorporated herein in their entirety.

Figure 8:
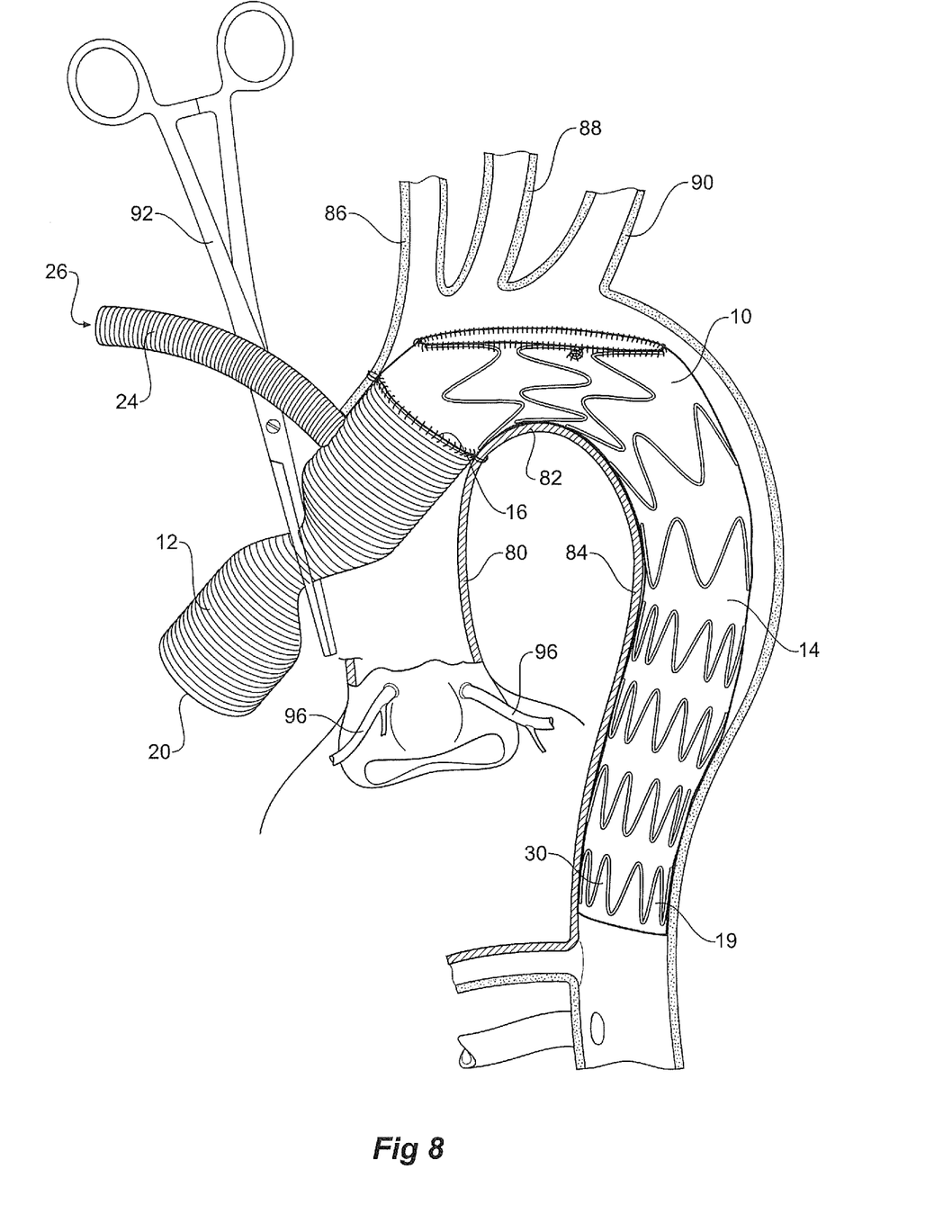
FIG. 8 shows one stage in the delivery of the hybrid stent graft according to the present invention.
Figure 9:
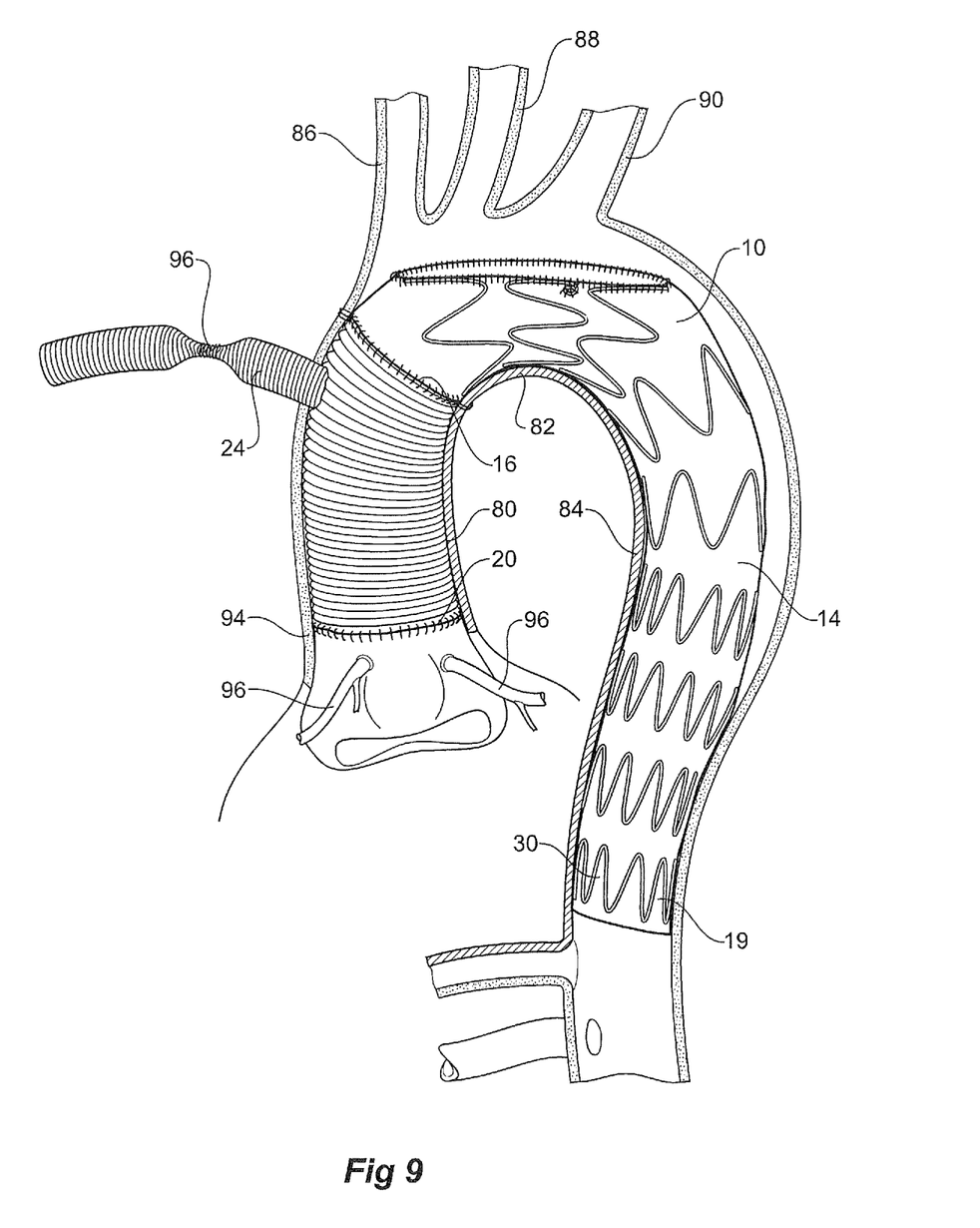
FIG. 9 shows a further stage in the delivery of the hybrid stent graft according to the present invention.

FIG. 8 shows one stage in the delivery of the hybrid stent graft according to one embodiment of the present invention and FIG. 9 shows a further stage in the delivery of the hybrid stent graft.

FIGS. 8 and 9 show an aortic arch of a patent in schematic form. The thoracic arch shown schematically comprises an ascending aorta 80 extending to the thoracic arch 82 and a descending aorta 84 from the thoracic arch. Substantially at the top of the thoracic arch but slightly to the ventral side of the arch the major vessels branch off the arch. The major vessels are the brachiocephalic artery 86, the common carotid artery 88 and the left subclavian 90.

A dissection has occurred in the ascending aorta 80 and open chest surgery has been performed to expose the aorta. The patient has been chilled and the heart slowed or stopped and an incision has been made into the ascending aorta and the introducer has been introduced into the aortic arch and down into the descending aorta and the hybrid stent graft has been released from the introducer and the introducer had been removed. The distal end 19 of the second portion 14 of the hybrid stent graft 10 has expanded under the action of the self expanding stents 30 and has sealed onto the wall of the descending aorta.

A clamp 92 has been placed onto the first tubular portion 12 and the junction 16 between the first and second portions has been stitched to the ascending aorta proximally of the brachiocephalic artery 86.

A bypass blood flow can then be established through the bypass lumen 26 of the temporary bypass tube 24 so that blood can again perfuse the aortic arch and the descending aorta. The pair of tubes 44 which defines the fluid flow path between the second lumen 28 and the recess lumen 35 allow blood flow into the recess and from there to the great arteries. The physician can then stitch the proximal end 20 of the first tubular portion to the sinotubular junction adjacent to the coronary arteries 96.

The clamp 92 can then be removed and temporary bypass tube 24 can be permanently closed off by stitching 96 or the like. Blood flow can then be re-established from the heart through the first tubular portion into the aortic arch and the descending aorta. The pair of tubes 44 which defines the fluid flow path between the second lumen 28 and the recess lumen 35 allow blood flow into the recess and from there to the great arteries. The physician may then stitch the original ascending aorta wall around the first tubular portion.

During the operation to install the device of the present invention and after the deployment device has been withdrawn, the brachiocephalic and left common carotid arteries can be catheterised and a side arm stent graft deployed into each using a simple delivery device deployed through the bypass lumen to provide a permanent flow path to the brachiocephalic and left common carotid arteries. At the same time an anastomosis can be provided between the left common carotid artery and the left subclavian to provide perfusion to both these arteries.

Alternatively, in a subsequent operation, the pair of tubes in the recess can be accessed with bridging covered stents from the brachiocephalic and left common carotid arteries to provide depressurization of the external portion of the stent graft. This will provide a more permanent flow path to the brachiocephalic and left common carotid arteries.

Figure 10:
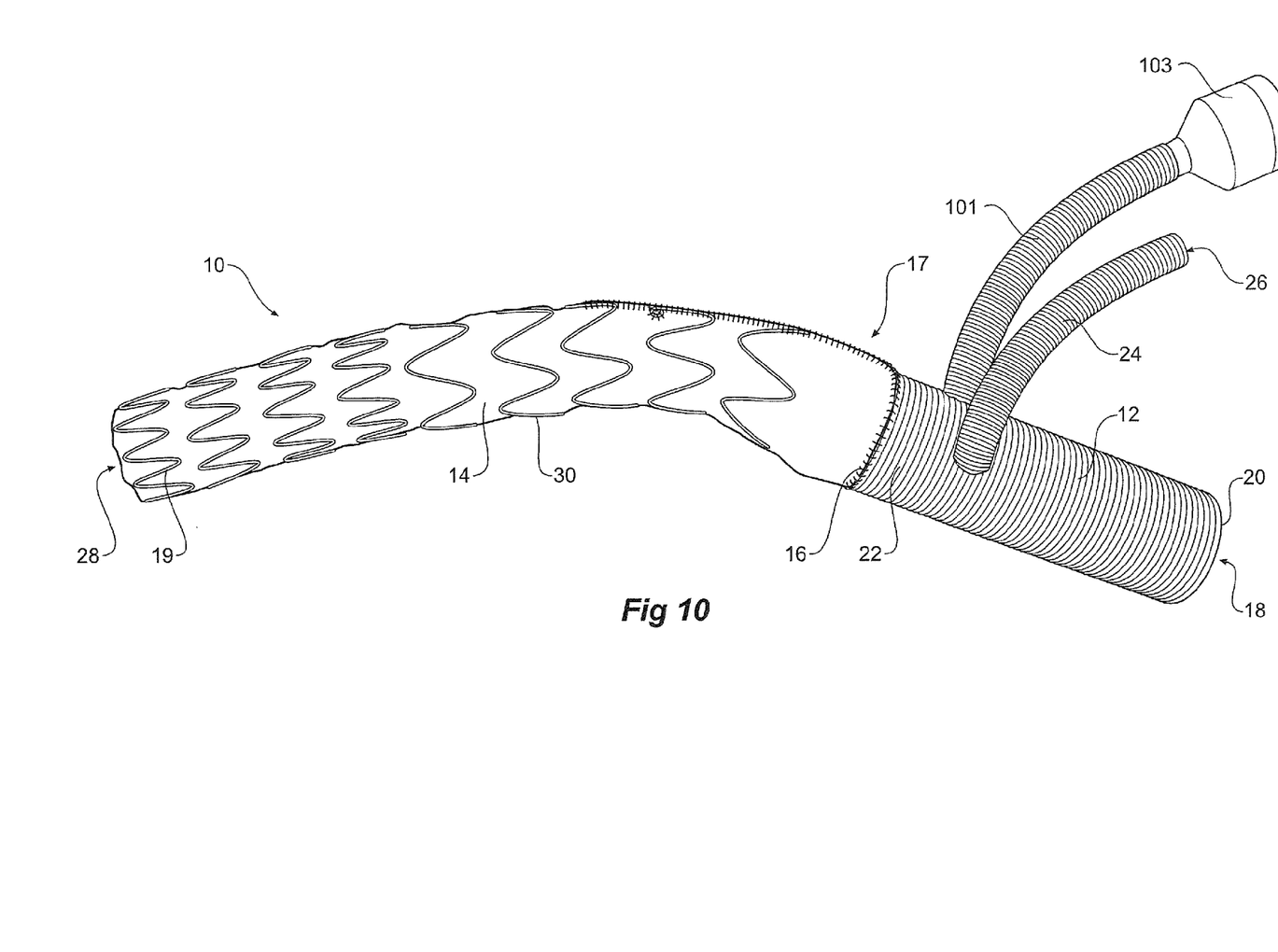
FIG. 10 shows a side view of an alternative embodiment of a hybrid stent graft according to the present invention.

FIG. 10 shows a side view of an alternative embodiment of a hybrid stent graft according to the present invention. In this embodiment the same reference numerals are used for corresponding items to those shown in FIG. 1.

In FIG. 10 the hybrid stent graft 10 comprises a first tubular portion 12 for placement into the ascending aorta of a patient and a second tubular portion 14 for extending around the thoracic arch and down the descending aorta. The first tubular portion 12 is connected to the second tubular portion 14 at a junction 16. The first tubular portion 12 comprises a tubular biocompatible graft material which defines a first lumen 18 therethrough. The first tubular portion 12 has a proximal end 20 and a distal end 22. The proximal end in use connects to the aorta substantially at the sinotubular junction and the distal end in use connects to the aorta proximally of the brachiocephalic artery (see FIGS. 8 and 9) such that in use the first tubular portion essentially replaces the ascending aorta of the patient.

A temporary bypass tube 24 of lesser diameter than the first tubular portion has a bypass lumen 26 through it. The bypass tube 24 extends from and is in fluid communication with the first tubular portion adjacent to the junction 16 between the first tubular portion and the second tubular portion. A second temporary tube 101 extends from and is in fluid communication with the first tubular portion adjacent to the junction 16 between the first tubular portion and the second tubular portion. The second temporary tube 101 has a haemoreduction valve 103 at its distal end. The haemoreduction valve 103 is used for deployment of delivery devices therethrough for placement of the bridging covered stents into the brachiocephalic and left common carotid arteries to provide depressurization of the external portion of the stent graft.

Both the first tubular portion 12 and the temporary bypass tube 24 are formed from a corrugated biocompatible material which is essentially impervious to blood. Such a material is a gelatine sealed knitter graft material sold under the trade mark Gelseal by Terumo CardioVascular Systems Corp MI, USA.

The second tubular portion 14 comprises a tubular biocompatible graft material and defines a second lumen 28 through it. A plurality of self expanding stents 30 along the tubular biocompatible graft material are fastened to and support the tubular biocompatible graft material. The second lumen 28 is in fluid communication with the first lumen 18 through the junction 16. The second tubular portion 14 has an elongate recess 32 defined by a recess wall 34 and thereby defines a recess lumen 35. The recess lumen is therefore outside of the second tubular portion. There is at least one aperture 35 in the recess wall defining a fluid flow path between the second lumen 28 and the recess lumen 35. The recess lumen is in use intended to engage an outer curve of the thoracic arch to enable blood flow from the second lumen 28 through the at least one aperture 36 into the recess lumen 35 and into the arteries of the thoracic arch (see FIGS. 8 and 9).

Before the operation is completed using the device of the present invention the pair of tubes 44 can be accessed through the second temporary tube to deploy bridging covered stents from each of the tubes into the brachiocephalic and left common carotid arteries to provide depressurization of the external portion of the stent graft. This will provide a more permanent flow path to the brachiocephalic and left common carotid arteries. Subsequently the second temporary tube can be closed off and the haemoreduction valve removed.

The invention claimed is:

1. A hybrid stent graft device comprising: a longitudinal axis;
   a first tubular graft portion and a second tubular graft portion different from and connected to the first tubular graft portion at a junction therebetween;
   the first tubular graft portion comprising a first biocompatible graft material and a first lumen therethrough;
   the second tubular graft portion comprising a second biocompatible graft material different from the first biocompatible graft material, a second lumen therethrough and a plurality of self expanding stents along the second tubular graft portion and fastened thereto;
   the second lumen being in fluid communication with the first lumen through the junction;
   the second tubular graft portion having an elongate recess, a resilient wire framework having a substantial boat shape and an open side having a rounded opening in a longitudinal direction and supporting the elongate recess, the elongate recess having a recess lumen outside the second tubular graft portion and a recess wall, at least one aperture in the recess wall, the open side of the framework adjacent the at least one aperture, and the recess lumen being in fluid communication with the second lumen through the at least one aperture in the recess wall.

2. A hybrid stent graft device as in claim 1 wherein the first tubular graft portion comprises a biocompatible corrugated gel seal material.

3. A hybrid stent graft device as in claim 1 wherein the at least one aperture in the recess wall comprises at least one short tube defining the fluid flow path between the second lumen and the recess lumen.

4. A hybrid stent graft device as in claim 3 comprising two short tubes in the recess wall defining fluid flow paths between the second lumen and the recess lumen.

5. A hybrid stent graft device as in claim 1 wherein the first tubular graft portion is unstented.

6. A hybrid stent graft device as in claim 1 wherein the recess is boat or bath shaped.

7. A hybrid stent graft device as in claim 1 wherein the resilient wire framework comprises a wire reinforcement structure attached to the recess wall.

8. A hybrid stent graft device as in claim 1 further comprising a temporary bypass tube, the temporary bypass tube including a bypass lumen having a diameter less than the diameter of the first lumen, the bypass tube extending from and in fluid communication with the first tubular graft portion adjacent to the junction between the first tubular graft portion and the second tubular graft portion.

9. A hybrid stent graft device as in claim 8 further comprising a second temporary tube, the second temporary tube extending from and in fluid communication with the first tubular graft portion adjacent to the junction between the first tubular graft portion and the second tubular graft portion.

10. A hybrid stent graft device as in claim 9 wherein the second temporary tube comprises a haemoreduction valve to allow access for a covered stent graft delivery device.

11. A hybrid stent graft in combination with an introducer comprising:
    the hybrid stent graft being as defined in claim 1;
    the introducer comprising a handle portion, and an introducer portion, the introducer portion comprising a pusher and a nose cone dilator at an end of the introducer portion,
    the hybrid stent graft being retained on the introducer with the introducer portion extending through the first tubular graft portion and the second tubular graft portion with the proximal end of the first tubular graft potion nearest the handle portion and a distal end of the second tubular graft portion being releasably retained to the pusher adjacent to the nose cone dilator.

12. A hybrid stent graft in combination with an introducer as in claim 11 wherein the second tubular graft portion comprises diameter reducing ties therealong and a release arrangement for the diameter reducing ties on the handle portion.

13. A hybrid stent graft in combination with an introducer as in claim 11 wherein the second tubular graft portion comprises a releasable spiral stabilizing wire engaging the second tubular graft portion to the pusher and a release arrangement for the releasable spiral stabilizing wire on the handle portion.

14. A hybrid stent graft in combination with an introducer as in claim 11 wherein the pusher comprises a preformed curve approximating the curvature of the thoracic arch.

15. A hybrid stent graft device comprising: a longitudinal axis;
    a first tubular graft portion comprising a first biocompatible graft material and a first lumen;
    a second tubular graft portion comprising a second biocompatible graft material different from the first biocompatible graft material, the second tubular graft portion connected to the first tubular graft portion at a junction and comprising a second lumen in fluid communication with the first lumen through the junction; and
    the second tubular graft portion having an elongate recess, a resilient wire framework having a substantial boat shape and an open side having a rounded opening in a longitudinal direction and supporting the elongate recess, the elongate recess having a recess lumen outside the second tubular graft portion and a recess wall, at least one aperture in the recess wall, the open side of the framework adjacent the at least one aperture, and the recess lumen being in fluid communication with the second lumen through the at least one aperture in the recess wall.

16. A hybrid stent graft device as in claim 15 further comprising a temporary bypass tube, the temporary bypass tube including a bypass lumen having a diameter less than the diameter of the first lumen, the bypass tube extending from and in fluid communication with the first tubular graft portion adjacent to the junction between the first tubular graft portion and the second tubular graft portion.

17. A hybrid stent graft device as in claim 16 wherein the first tubular graft portion is unstented.

18. A hybrid stent graft device as in claim 17 wherein the at least one aperture in the recess wall comprises at least one short tube.

19. A hybrid stent graft device as in claim 18 wherein the recess is boat or bath shaped.

20. A hybrid stent graft device comprising: a longitudinal axis;
- a first tubular graft portion and a second tubular graft portion different from and connected to the first tubular graft portion at a junction therebetween;
- the first tubular graft portion comprising a first biocompatible graft material and a first lumen therethrough, the first lumen having a first diameter;
- a temporary bypass tube comprising a bypass lumen therethrough, the bypass lumen having a diameter less than the first diameter, the bypass tube extending from and in fluid communication with the first tubular graft portion adjacent to the junction between the first tubular graft portion and the second tubular graft portion;
- the second tubular graft portion comprising a second biocompatible graft material different from the first biocompatible graft material, a second lumen therethrough, and a plurality of self expanding stents along the second biocompatible graft material and fastened thereto;
- the second lumen being in fluid communication with the first lumen through the junction;
- the second tubular graft portion having an elongate recess, a resilient wire framework having a substantial boat shape and an open side having a rounded opening in a longitudinal direction and supporting the elongate recess, the elongate recess having a recess lumen outside the second tubular graft portion and a recess wall, at least one aperture in the recess wall, the open side of the framework adjacent the at least one aperture, and the recess lumen being in fluid communication with the second lumen through the at least one aperture in the recess wall.

\* \* \* \* \*